United States Patent
Miyasa et al.

(10) Patent No.: US 11,437,136 B2
(45) Date of Patent: Sep. 6, 2022

(54) IMAGE PROCESSING APPARATUS, IMAGE PROCESSING METHOD, AND STORAGE MEDIUM

(71) Applicant: CANON KABUSHIKI KAISHA, Tokyo (JP)

(72) Inventors: Kazuhiro Miyasa, Narashino (JP); Toru Tanaka, Funabashi (JP); Kiyohide Satoh, Kawasaki (JP); Yoshio Iizuka, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 113 days.

(21) Appl. No.: 16/907,058

(22) Filed: Jun. 19, 2020

(65) Prior Publication Data
US 2020/0411166 A1 Dec. 31, 2020

(30) Foreign Application Priority Data
Jun. 26, 2019 (JP) .............................. JP2019-119130

(51) Int. Cl.
*G16H 30/40* (2018.01)
*G16H 30/20* (2018.01)
(Continued)

(52) U.S. Cl.
CPC ........... *G16H 30/40* (2018.01); *G06T 3/0068* (2013.01); *G06T 5/50* (2013.01); *G06T 11/006* (2013.01);
(Continued)

(58) Field of Classification Search
CPC ...... G16H 30/40; G16H 30/20; G06T 3/0068; G06T 5/50; G06T 11/006;
(Continued)

(56) References Cited

U.S. PATENT DOCUMENTS

| | | | |
|---|---|---|---|
| 8,605,970 B2 * | 12/2013 | Bar-Aviv | G06T 5/002 382/128 |
| 2010/0266188 A1 * | 10/2010 | Burns | G06T 7/30 382/132 |

(Continued)

OTHER PUBLICATIONS

R. Sakamoto, et al., "Temporal subtraction system for detecting bone metastasis using LDDMM: preliminary study", Jun. 2014, Japan.

*Primary Examiner* — Vu Le
*Assistant Examiner* — Julius Chai
(74) *Attorney, Agent, or Firm* — Canon U.S.A., Inc. IP Division

(57) ABSTRACT

An image processing apparatus includes an acquisition unit configured to acquire a first medical image and a second medical image that are three-dimensional images obtained by imaging a subject, a determination unit configured to determine a first resolution based on a resolution of the first medical image and determine a second resolution based on a predetermined resolution, a first generation unit configured to generate a first subtraction image having the first resolution by performing a first subtraction process between the first and second medical images, and generate a second subtraction image having the second resolution by performing a second subtraction process between the first and second medical images, and a second generation unit configured to generate a projection image using the second subtraction image.

22 Claims, 6 Drawing Sheets

(51) Int. Cl.
*G06T 3/00* (2006.01)
*G06T 11/00* (2006.01)
*G06T 5/50* (2006.01)

(52) U.S. Cl.
CPC ... *G16H 30/20* (2018.01); *G06T 2207/10072* (2013.01); *G06T 2207/20016* (2013.01); *G06T 2207/20224* (2013.01); *G06T 2210/41* (2013.01)

(58) Field of Classification Search
CPC . G06T 2207/10072; G06T 2207/20016; G06T 2207/20224; G06T 2210/41
See application file for complete search history.

(56) References Cited

U.S. PATENT DOCUMENTS

| | | | |
|---|---|---|---|
| 2011/0274330 A1* | 11/2011 | Mori | A61B 6/5235 382/131 |
| 2011/0305405 A1* | 12/2011 | Kawamura | G06T 7/337 382/294 |
| 2015/0221077 A1* | 8/2015 | Kawabata | G06T 7/001 382/141 |
| 2017/0061612 A1* | 3/2017 | Mizobe | G06T 11/003 |
| 2017/0178307 A1* | 6/2017 | Yan | G06T 5/50 |
| 2020/0058098 A1* | 2/2020 | Hirakawa | G06T 7/97 |

* cited by examiner

IMAGE PROCESSING APPARATUS, IMAGE PROCESSING METHOD, AND STORAGE MEDIUM

BACKGROUND OF THE INVENTION

Field of the Invention

The present invention relates to an image processing apparatus, an image processing method, and a storage medium.

Description of the Related Art

In the medical field, an attempt is made to visualize changes over time in a lesion by presenting to a user a subtraction image generated from two images captured at different times from each other by various modalities.

Non-patent literature (R. Sakamoto, et al., Temporal subtraction system for detecting bone metastasis using LDDMM: preliminary study, CARS 2014) discusses a technique for displaying as a two-dimensional tomographic image a subtraction image generated from two three-dimensional images captured by a computed tomography (CT) apparatus. The non-patent literature also discusses a technique for generating and displaying a two-dimensional projection image obtained by projecting the intensity value (pixel value) of the subtraction image in a direction parallel to a slice plane (generally, a direction orthogonal to the body axis of a subject in CT).

In the techniques discussed in the above non-patent literature, however, in a case where a subtraction image is generated from two three-dimensional images (original images) having coarse slice intervals (pixel sizes in the body axis direction), the slice interval of the subtraction image is also coarse. As a result, in a case where a projection image obtained by projecting the intensity value (pixel value) of the subtraction image in a direction parallel to the slice plane is displayed on a display unit, the resolution of the projection image is more coarse than that of the tomographic image displayed on the display unit. Thus, it is difficult for a user to observe changes over time in a lesion.

SUMMARY OF THE INVENTION

The present invention is directed to generating a subtraction image having an appropriate resolution according to a cross section to be displayed. The present invention is not only directed to the above, but can also be directed to obtaining an operation and an effect that result from the configurations illustrated in the description of the embodiments below and cannot be obtained by a conventional technique.

According to an aspect of the present invention, an image processing apparatus includes an acquisition unit configured to acquire a first medical image and a second medical image that are three-dimensional images obtained by imaging a subject, a determination unit configured to determine a first resolution based on a resolution of the first medical image and determine a second resolution based on a predetermined resolution, a first generation unit configured to generate a first subtraction image having the first resolution by performing a first subtraction process between the first and second medical images, and generate a second subtraction image having the second resolution by performing a second subtraction process between the first and second medical images, and a second generation unit configured to generate a projection image using the second subtraction image.

Further features of the present invention will become apparent from the following description of exemplary embodiments with reference to the attached drawings.

DESCRIPTION OF THE EMBODIMENTS

With reference to the attached drawings, exemplary embodiments of an image processing apparatus according to the present invention will be described in detail below. The components described in these exemplary embodiments, however, are merely illustrative. The technical scope of the image processing apparatus according to the present invention is determined by the appended claims, and is not limited by the following individual exemplary embodiments. The present invention is not limited to the following exemplary embodiments. Various modifications (including the organic combinations of the exemplary embodiments) can be made based on the spirit of the present invention, and are not excluded from the scope of the present invention. That is, all the configurations obtained by combining the following exemplary embodiments and their variations are also included in the exemplary embodiments of the present invention.

Figure 5:
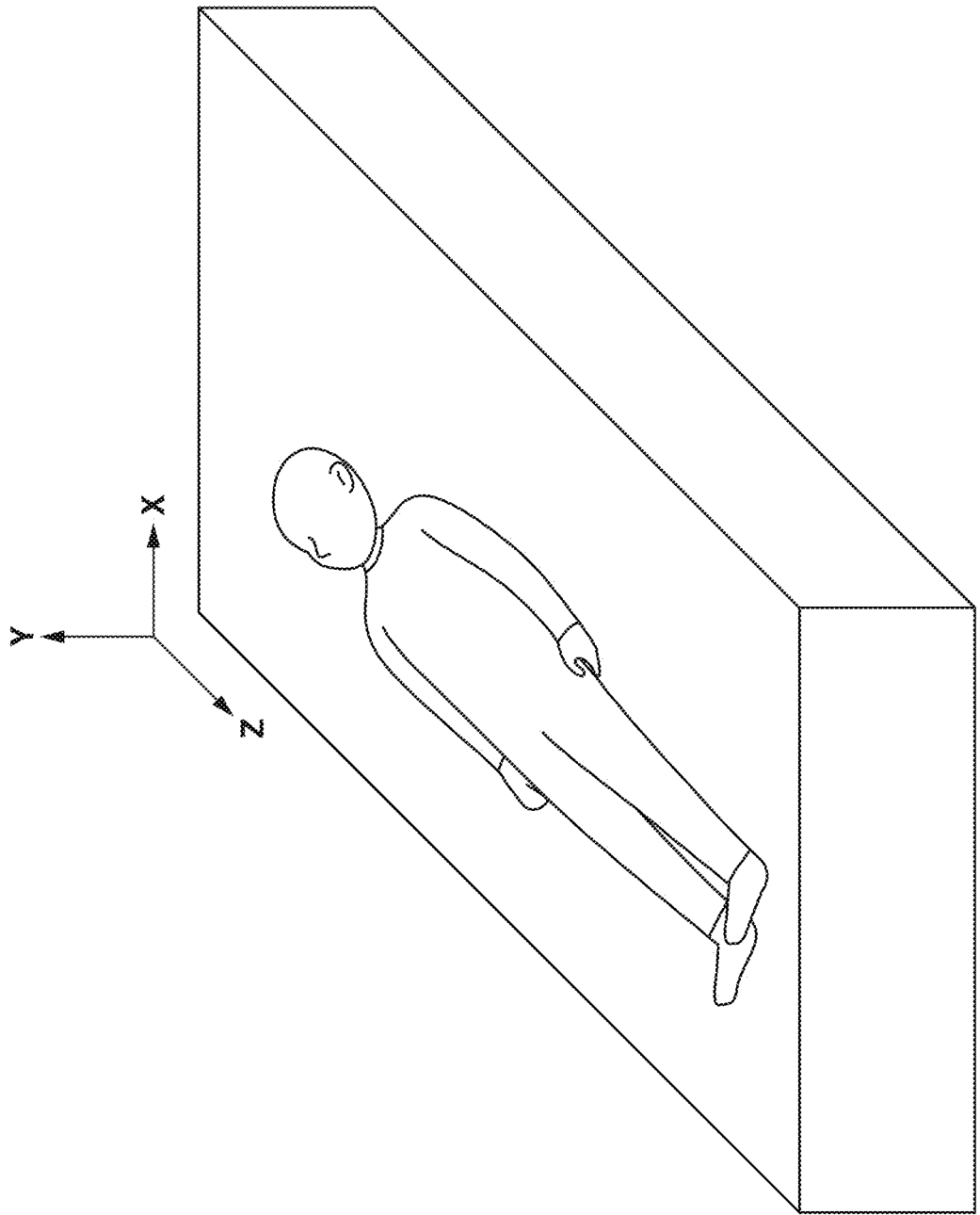
FIG. 5 is a diagram illustrating settings of coordinate axes according to the present exemplary embodiment.

In the specification, as illustrated in FIG. 5, an axis representing the direction from the right hand to the left hand of a subject in a supine position is defined as an X-axis. An axis representing the direction from the back side to the front side of the subject is defined as a Y-axis. An axis representing the direction from the head to the feet of the subject is defined as a Z-axis. Further, an XY cross section is defined as an axial plane. A YZ cross section is defined as a sagittal plane. A ZX cross section is defined as a coronal plane. That is, the X-axis direction is a direction orthogonal to the sagittal plane (hereinafter, a "sagittal direction"). The Y-axis direction is a direction orthogonal to the coronal plane (hereinafter, a "coronal direction"). Further, the Z-axis direction is a direction orthogonal to the axial plane (hereinafter, an "axial direction"). Particularly in the case of a computed tomography (CT) image configured as a set of two-dimensional tomographic images (slice images), the slice plane of the image represents the axial plane. That is, in this case, the axial direction represents a direction orthogonal to the slice plane (hereinafter, a "slice direction"). The method for setting the coordinate system is merely an example, and the coordinate system may be defined by a method other than this method.

An image processing apparatus according to a first exemplary embodiment is an apparatus that performs registration between two images captured at different times from each other, thereby generating a subtraction image. An "image" in the present exemplary embodiment includes not only the image that is displayed on a display unit, but also the image that is stored as image data in a database or a storage unit.

Figure 3:
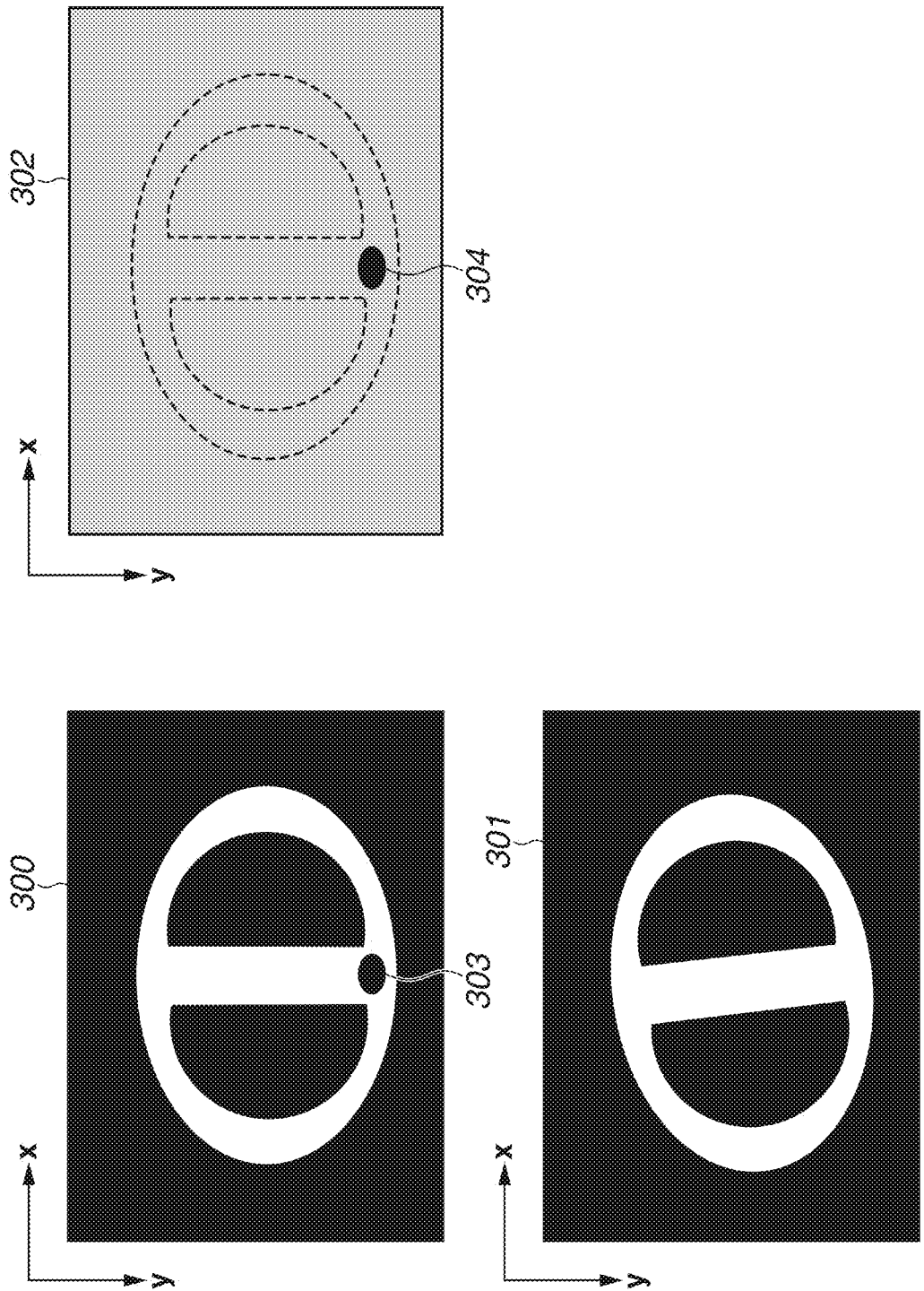
FIG. 3 is a diagram illustrating axial cross sections of original images and a subtraction image.
Figure 4:
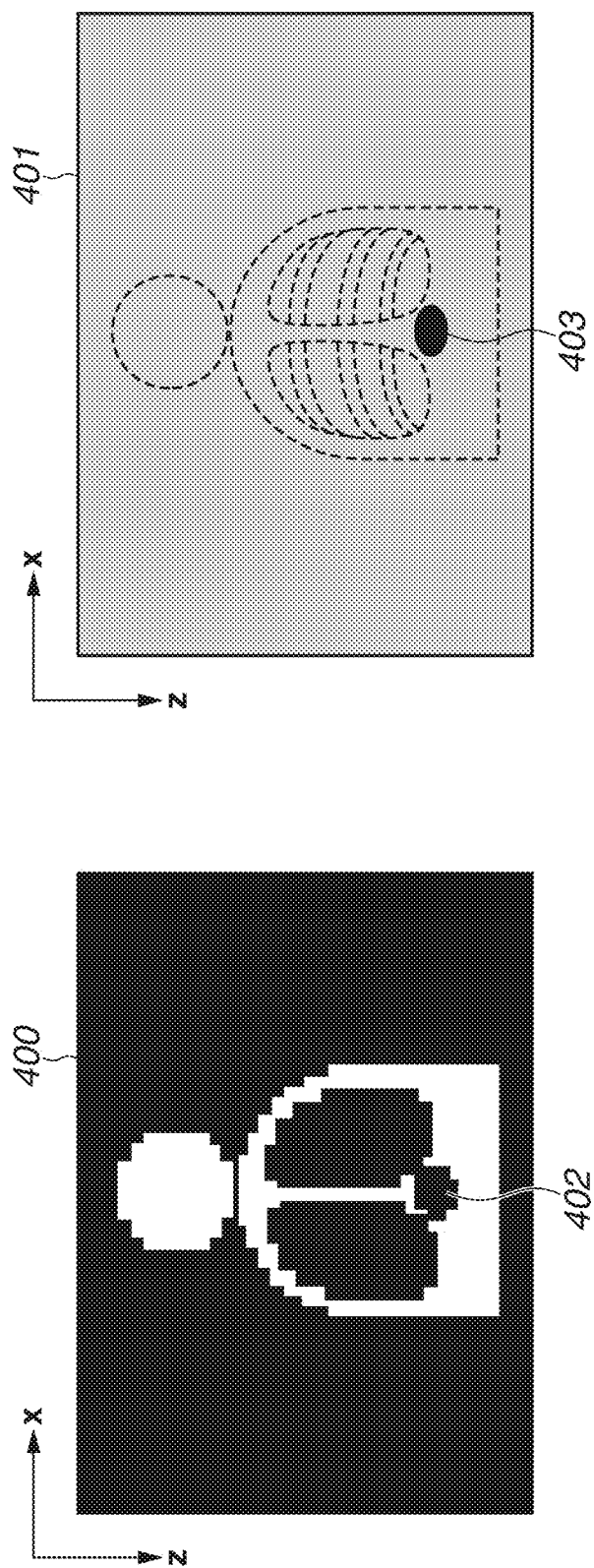
FIG. 4 is a diagram illustrating a coronal cross section of an original image and a subtraction projection image.

The image processing apparatus according to the present exemplary embodiment is characterized by generating two types of subtraction images, namely a subtraction image (a first subtraction image) to be displayed in a cross-sectional manner as illustrated in FIG. 3, and a subtraction image (a second subtraction image) to be displayed in a projected manner as illustrated in FIG. 4. More specifically, the image processing apparatus generates as the first subtraction image a subtraction image obtained by matching the slice interval of the subtraction image to that of an image as a reference for registration between two images (original images). The image processing apparatus generates as the second subtraction image a subtraction image obtained by setting the slice interval of the subtraction image to a sufficiently fine resolution.

With reference to FIGS. 1 to 4, the configuration and the processing according to the present exemplary embodiment are described below.

Figure 1:
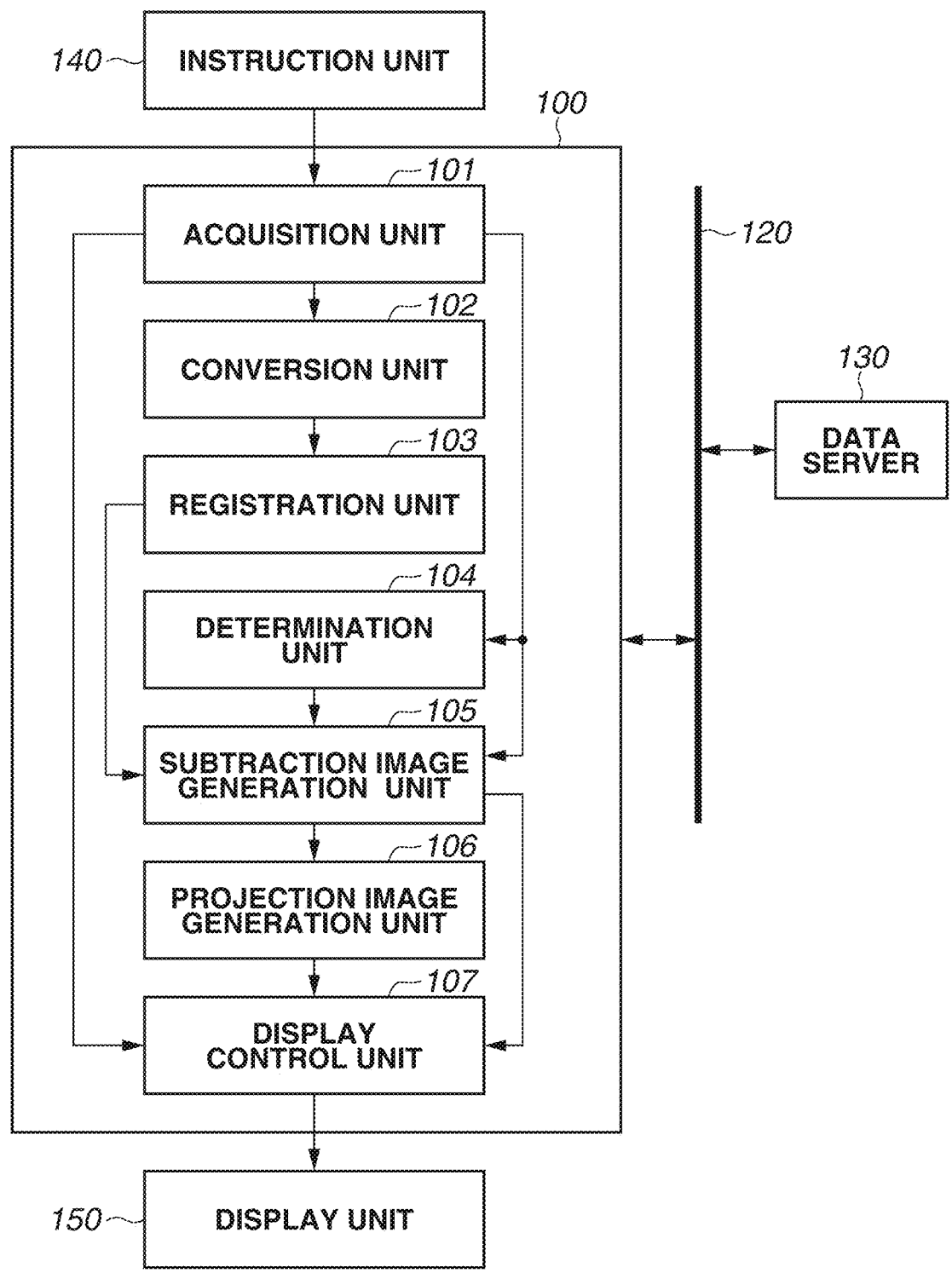
FIG. 1 is a diagram illustrating an example of a device configuration of an image processing system according to a first exemplary embodiment.

FIG. 1 illustrates the configuration of an image processing system according to the present exemplary embodiment. As illustrated in FIG. 1, an image processing apparatus 100 according to the present exemplary embodiment is connected to a data server 130 via a network 120.

The data server 130 holds a plurality of medical images. For example, the data server 130 is a picture archiving and communication system (PACS) that receives medical image data captured by a modality and stores and manages the medical image data via a network. In the following description, the data server 130 holds, as a first medical image and a second medical image, a plurality of three-dimensional tomographic images obtained by imaging the subject in advance in different conditions (different modalities, different imaging modes, different dates and times, and different postures). The present exemplary embodiment is described on the assumption that the first and second medical images are three-dimensional tomographic images (three-dimensional medical images) captured by X-ray CT apparatuses.

The modalities for capturing three-dimensional tomographic images may be a magnetic resonance imaging (MRI) apparatus, a three-dimensional ultrasonic imaging apparatus, a photoacoustic tomography apparatus, a positron emission tomography (PET) apparatus, a single-photon emission computed tomography (SPECT) apparatus, or an optical coherence tomography (OCT) apparatus. Further, the first and second medical images may be any images so long as the first and second medical images are three-dimensional tomographic images from which a subtraction image is generated. For example, the first and second medical images may be images captured in the same period by different modalities or in different imaging modes. Alternatively, the first and second medical images may be images obtained by imaging the same patient in the same posture using the same modality at different dates and times for a follow-up. The first and second medical images are three-dimensional medical images (three-dimensional tomographic images) configured as a set of two-dimensional tomographic images. The position and the orientation of each two-dimensional tomographic image are converted to those in a reference coordinate system (a coordinate system in a space based on the subject) and then held in the data server 130. At this time, the first and second medical images represented in the reference coordinate system are input to the image processing apparatus 100 according to an instruction from a user operating an instruction unit 140.

The image processing apparatus 100 is an apparatus that receives from the instruction unit 140 a request to perform processing, made by the user, performs image processing, and outputs the processing result to a display unit 150. For example, the image processing apparatus 100 functions as a terminal apparatus for radiographic interpretation that is operated by the user such as a doctor. Specifically, based on an instruction from the user through the instruction unit 140, the image processing apparatus 100 acquires a first medical image and a second medical image to be subjected to image processing, as a pair of images from the data server 130. Then, the image processing apparatus 100 performs a registration process between these images, generates a subtraction image, and outputs the subtraction image to the display unit 150. The image processing apparatus 100 includes as its functional components an acquisition unit 101, a conversion unit 102, a registration unit 103, a determination unit 104, a subtraction image generation unit 105, a projection image generation unit 106, and a display control unit 107.

The acquisition unit 101 acquires information regarding the first and second medical images input to the image processing apparatus 100. The conversion unit 102 performs resolution conversion on each of the first and second medical images to a resolution determined in advance (hereinafter, a "processing resolution"). The registration unit 103 performs a registration process between the first and second medical images subjected to the resolution conversion (hereinafter, a "first conversion image" and a "second conversion image", respectively) and calculates a displacement field between the images. The determination unit 104 determines the resolution of a subtraction image to be output (hereinafter, an "output resolution"). Based on the output resolution, the subtraction image generation unit 105 generates a subtraction image between a second deformation image obtained by deforming the second medical image to match the first medical image based on the acquired displacement field, and the first medical image. The projection image generation unit 106 generates a projection image (hereinafter, a "subtraction projection image") obtained by two-dimensionally projecting the intensity value (pixel value) of the subtraction image. The display control unit 107 performs control to output the generated subtraction image and subtraction projection image or the like to the display unit 150.

The display unit 150 includes any device such as a liquid crystal display (LCD) or a cathode ray tube (CRT) and displays a medical image for the doctor to perform radiographic interpretation. Specifically, the display unit 150 displays cross-sectional images of the first and second medical images acquired from the image processing apparatus 100. The display unit 150 displays a cross-sectional image of the subtraction image generated by the image processing apparatus 100 and the subtraction projection image generated by the image processing apparatus 100.

Figure 2:
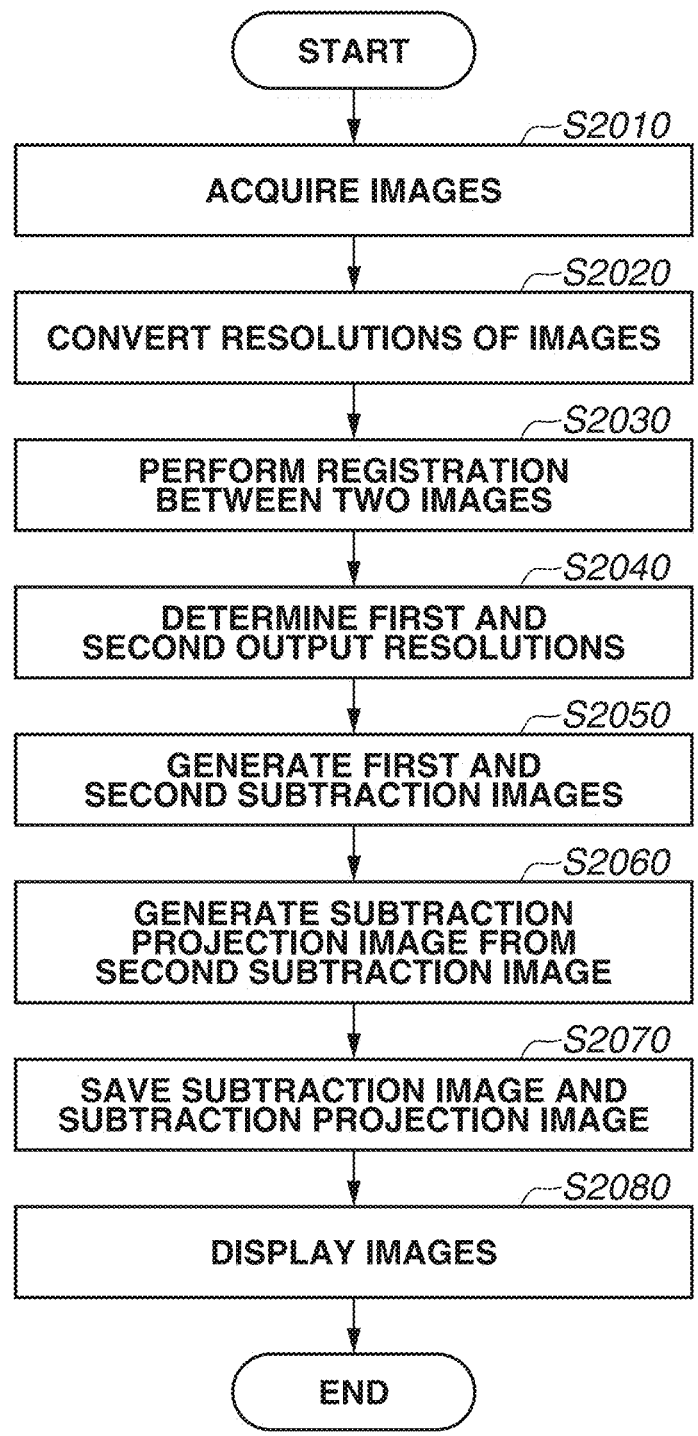
FIG. 2 is a flowchart illustrating an example of an entirety of a processing procedure according to the first exemplary embodiment.

FIG. 2 is a flowchart illustrating the entirety of a processing procedure performed by the image processing apparatus 100.

(Acquisition of Images)

In step S2010, the acquisition unit 101 acquires from the data server 130 a first medical image and a second medical image specified by the user through the instruction unit 140. That is, the acquisition unit 101 corresponds to an example of an acquisition unit configured to acquire a first medical image and a second medical image that are three-dimensional images obtained by imaging a subject. Then, the acquisition unit 101 outputs the first and second medical images to the conversion unit 102, the determination unit 104, the subtraction image generation unit 105, and the display control unit 107.

(Resolution Conversion on Images)

In step S2020, the conversion unit 102 performs resolution conversion on the first and second medical images to the processing resolution, thereby acquiring a first conversion image and a second conversion image. For example, the conversion unit 102 acquires a first conversion image and a second conversion image having pixel sizes made isotropic so that if the pixel sizes of the first and second medical images as original images of a subtraction image are anisotropic, registration between the images in the subsequent process can be performed with high accuracy. More specifically, for example, in a case where the first and second medical images are CT images, the resolutions in the slice plane (e.g., in the sagittal direction and the coronal direction) are higher than the resolution in the slice direction (the axial direction). Thus, the process of upsampling pixels in the slice direction according to the resolutions in the slice plane is performed. More specifically, for example, if the resolutions in the slice plane (the resolution in the X-axis direction and the resolution in the Y-axis direction) are 1 mm, and the resolution in the slice direction (the resolution in the Z-axis direction) is 3 mm, the resolution in the slice direction is upsampled from 3 mm to 1 mm. A known image processing technique can be used to interpolate the density values when the resolution conversion is performed.

In the present exemplary embodiment, the processing resolution is set to 1 mm in each of the three-dimensional axis directions so that the subtraction in detail between images can be calculated. Then, a first conversion image and a second conversion image having pixel sizes made isotropic by the resolution conversion are acquired. The processing resolution may not be 1 mm so long as the resolution enables the sufficient calculation of the subtraction in detail between images. The pixel sizes may not necessarily be made isotropic so long as the resolutions can be converted to such an extent that registration between the images in the subsequent process can be performed with high accuracy. Further, in a case where the resolution conversion process is not necessary, such as a case where the resolutions of the first and second medical images are already the processing resolution when the first and second medical images are acquired in step S2010, the resolution conversion may not necessarily be performed. Then, the conversion unit 102 outputs the generated first and second conversion images to the registration unit 103.

(Registration Between Two Images)

In step S2030, the registration unit 103 performs registration between the first and second conversion images so that pixels representing the same part approximately match each other, and acquires a displacement field associating positions between the images. That is, the registration unit 103 corresponds to an example of a registration unit configured to perform registration between the first and second medical images subjected to resolution conversion. Then, the registration unit 103 outputs information regarding the displacement field as the result of the registration to the subtraction image generation unit 105.

In the present exemplary embodiment, registration between images refers to the process of calculating a displacement field for displacing each pixel position on one image to a corresponding pixel position on the other image. For example, in a case where there are two images captured at different times from each other, then with respect to each pixel position on one image as a reference, a corresponding pixel position on the other image is estimated, thereby calculating a displacement field from the one image as the reference to the other image. That is, in the present exemplary embodiment, if the first medical image is a reference, a pixel position on the second conversion image corresponding to each pixel position on the first conversion image is obtained, thereby acquiring a displacement vector at each pixel position. That is, the generated displacement field is an image that stores a displacement vector at each pixel position on the first conversion image to a corresponding position on the second conversion image. This image has the same resolution and the same number of pixels as the first conversion image. Thus, if the processing resolution is 1 mm in each of the X-axis, Y-axis, and Z-axis directions, the displacement field is also a displacement vector field having a resolution of 1 mm in each of the X-axis, Y-axis, and Z-axis directions. Consequently, the displacement field holds the amount of information that enables the calculation of the subtraction in detail between images.

In the present exemplary embodiment, registration is performed by a known image processing technique. For example, registration is performed by deforming one of images so that the similarity between the images is high. As the similarity between the images, any of known methods such as the sum of squared differences (SSD), mutual information, and a cross-correlation coefficient, which are generally used, can be employed. As a model for the deformation of the image, a deformation model based on a radial basis function such as a thin plate spline (TPS) or a known deformation model based on free-form deformation (FFD) or large deformation diffeomorphic metric mapping (LDDMM) can be used.

(Determination of First and Second Output Resolutions)

In step S2040, the determination unit 104 determines a first output resolution (a first resolution) and a second output resolution (a second resolution) based on the resolution of the first medical image and the processing resolution used in step S2020. Then, the determination unit 104 outputs the values of the determined output resolutions to the subtraction image generation unit 105.

A description is given of the details of the process in which the determination unit 104 determines the first and second output resolutions. As a general method for generating a subtraction image between two images, there is a method for generating a subtraction image such that positions are associated with each other between an image as a reference for registration (the first medical image in the present exemplary embodiment) between two images, and the subtraction image with respect to each pixel. At this time, the subtraction image is generated with the same resolution as the image as the reference for registration (the first medical image). In the range where the subtraction image is generated, the subtraction image is generated with the same number of pixels as the image as the reference for registration (the first medical image). Consequently, for example, to confirm a position on a two-dimensional tomographic image included in the first medical image and a position on a two-dimensional tomographic image included in the subtraction image in association with each other, it is possible to easily display these positions in association with each other.

However, in a case where a subtraction projection image or a volume rendering image obtained by two-dimensionally projecting the subtraction image in a direction parallel to the slice plane, or a cross-sectional image obtained by cutting the subtraction image at any cross section including the sagittal plane or the coronal plane different from the slice plane (the axial plane) (hereinafter, the "subtraction projection image or the like") is generated and displayed, the following issue arises.

That is, since the subtraction image is generated with the same resolution as the image as the reference for registration (the first medical image), if the slice interval of the first medical image is coarse, the slice interval of the subtraction image is also coarse. Thus, in a case where the subtraction projection image or the like is displayed on the display unit 150, the subtraction projection image or the like is displayed with a coarse resolution in the slice direction as compared with a case where a cross-sectional image on the slice plane of the subtraction image is displayed on the display unit 150. This issue arises because, in a case where three-dimensional tomographic images are acquired by various modalities, the resolutions in all the axis directions often do not necessarily match each other. For example, in the case of an X-ray CT apparatus, to reduce the exposure dose and reduce the amount of data, the resolution in the slice direction (the axial direction) (the slice interval) is often more coarse than the resolution in a direction in the slice plane (e.g., the sagittal direction or the coronal direction) (the resolution in the slice plane).

In response, in the present exemplary embodiment, two types of subtraction images, namely a first subtraction image having a first output resolution suitable for cross section display and a second subtraction image having a second output resolution suitable for displaying the subtraction projection image or the like, are generated. Consequently, both in a case where a subtraction image is displayed in a cross-sectional manner and a case where a subtraction image is displayed in a projected manner, it is possible to observe the images with appropriate resolutions.

In this step, the determination unit 104 sets the first output resolution to be the same as the resolution of the first medical image. The determination unit 104 sets slice positions in the first subtraction image such that all the slice positions in the first subtraction image correspond to slice positions in the first medical image. Consequently, it is possible to easily display the first medical image and the first subtraction image in a cross-sectional manner such that the slices of the first medical image and the first subtraction image correspond to each other. The first output resolution is merely an example, and may not necessarily be the same as the resolution of the first medical image, and may only need to be a resolution that enables the display of the first medical image and the first subtraction image in a cross-sectional manner so that the slices of the first medical image and the first subtraction image correspond to each other. That is, the determination unit 104 corresponds to an example of a determination unit configured to determine a first resolution based on a resolution of the first medical image.

Meanwhile, the determination unit 104 sets the second output resolution to a sufficiently fine value so that the subtraction projection image or the like is not coarse. That is, the determination unit 104 determines the second output resolution as a resolution suitable for displaying a projection image generated by projecting the second subtraction image in a direction orthogonal to the body axis of the subject. For example, the determination unit 104 determines the second output resolution based on the resolution of the first medical image and a predetermined resolution that enables the calculation of the subtraction in detail between images. More specifically, the determination unit 104 sets the predetermined resolution as the upper limit of the second output resolution (hereinafter, an "upper limit resolution"). Then, regarding the resolution in each of the X-axis, Y-axis, and Z-axis directions, the determination unit 104 sets the higher (finer) of the two resolutions, namely the resolution of the first medical image and the upper limit resolution, as the second output resolution. That is, in each axis direction, if the resolution of the first medical image is "more coarse than the upper limit resolution", the determination unit 104 sets the second output resolution to a resolution that is the same as the upper limit resolution. On the other hand, in each axis direction, if the resolution of the first medical image is "the same as or finer than the upper limit resolution", the determination unit 104 sets the second output resolution to a resolution that is the same as the resolution of the first medical image. In other words, to prevent the resolution from being coarse in each axis direction, the determination unit 104 determines the second output resolution as a resolution obtained by correcting the resolution of the first medical image as a reference for the subtraction image, based on the upper limit resolution as a resolution that enables the visualization of the subtracted value regarding details (so that the resolution of the first medical image is not more coarse than the upper limit resolution).

As described above, the upper limit (the maximum value) is set for the value of the resolution in each axis direction of the second output resolution, whereby, even in a case where the resolution of the first medical image is coarse (the slice interval is coarse in many cases), the resolution in each axis direction of the subtraction projection image or the like can be made fine.

Further, in a case where the resolution of the first medical image is originally fine, i.e., in a case where the resolution of the first medical image is originally higher than the upper limit resolution, the resolution in each axis direction of the subtraction projection image or the like can be made fine as it is according to the first medical image. Thus, it is possible to determine a more appropriate resolution according to the resolution of the first medical image than a method for generating a subtraction image with a predetermined resolution regardless of the resolution of the first medical image. Thus, it is possible to generate the subtraction projection image or the like with high visibility.

Alternatively, the value of the processing resolution used in the resolution conversion for registration between the images in the subsequent process in step S2020 may be used as the upper limit resolution. Specifically, if the processing resolution is 1-mm isotropy, 1-mm isotropy is used as the upper limit resolution. That is, for example, if the resolution in the slice direction of the first medical image is 5 mm, the resolution of the first medical image is more coarse than the processing resolution in the slice direction. Thus, the value of the second output resolution in the slice direction is set to 1 mm. If, on the other hand, the resolution in the slice direction of the first medical image is 0.5 mm, the resolution of the first medical image is finer than the processing resolution in the slice direction. Thus, the value of the second output resolution in the slice direction is set to 0.5 mm.

As described above, the upper limit of the resolution (the upper limit resolution) in each axis direction of the second output resolution is matched to the processing resolution, whereby, as described in step S2030, the upper limit resolution also matches the resolution of the displacement field obtained by the registration process. As described in step S2030, the displacement field is generated with a resolution (e.g., 1 mm) that enables the calculation of the subtraction in detail between images. Thus, the upper limit in each axis direction of the second output resolution is not only merely set such that the size of each pixel on the subtraction projection image is not large, but also set to an appropriate value as the amount of information that enables the representation of the subtraction in detail between images.

The value used as the upper limit resolution is merely an example, and is not limited to the above. That is, the upper limit resolution may not match the value of the processing resolution. For example, a value obtained based on the processing resolution may be set as the upper limit resolution. For example, a value obtained by multiplying the processing resolution by a predetermined constant may be set as the upper limit resolution. For example, 1.5 is set as the predetermined constant, and if the processing resolution is 1 mm, the upper limit resolution can be set to 1.5 mm. As the predetermined constant, a value that enables the display of the subtraction projection image or the like with a sufficient sense of resolution can be empirically set. The predetermined constant is set to be greater than or equal to 1, whereby it is possible to speed up the generation of a subtraction image. Alternatively, a constant determined in advance may be set as the upper limit resolution. It is desirable that the upper limit resolution should have a predetermined value greater than or equal to 0.5 mm and less than or equal to 2.0 mm as a resolution that is not unnecessarily fine and enables the sufficient visualization of a fine subtracted value as in a small lesion.

The method for determining the second output resolution is not limited to the above. For example, the determination unit 104 may determine the second output resolution based on not only the combination of the two resolutions, namely the resolution of the first medical image and the upper limit resolution, but also the combinations of three resolutions further including the value of the resolution of the second medical image. In a more limited manner, the smallest value among those of the three resolutions may be set. Consequently, the second output resolution can be matched to the resolution having the greatest amount of information among the resolution of the first medical image, the resolution of the second medical image, and the upper limit resolution. In a case where the resolution of the second medical image is the highest, it is possible to generate a subtraction projection image or the like having a greater amount of information than in a case where the second output resolution is determined based on the two resolutions, namely the resolution of the first medical image and the upper limit resolution.

The second output resolution is not necessarily determined based on both the resolution of the first medical image and the upper limit resolution. Alternatively, the upper limit resolution may be set as it is as the second output resolution. That is, the determination unit 104 corresponds to an example of a determination unit configured to determine a second resolution based on a predetermined resolution. In this case, the second output resolution is not a resolution according to the resolution of the first medical image as described above, but the process of comparing resolutions to set the second output resolution is not necessary. Thus, it is possible to set a resolution having minimum fineness at low calculation cost. Further, the effect of speeding up the generation of a subtraction image is obtained.

The second output resolution does not necessarily need to be determined based on both the resolution of the first medical image and the upper limit resolution in all the three axis directions, namely the X-axis, Y-axis, and Z-axis directions. Alternatively, the second output resolution may be determined based on both the resolution of the first medical image and the upper limit resolution in only some predetermined axis directions. For example, the resolution in the XY plane (in the slice plane) may be matched to the resolution of the first medical image, and the value of the higher of the resolution of the first medical image and the upper limit resolution may be employed in only the Z-direction (the slice direction). Consequently, since the resolution in the slice plane of a CT image are generally finer than 1 mm, a fine resolution can be set as the resolution in the XY plane without comparing the resolutions in the XY plane with the upper limit resolution. Thus, in all the X-axis, Y-axis, and Z-axis directions, it is possible to set a resolution that is approximately the same as a resolution determined based on both the resolution of the first medical image and the upper limit resolution at low calculation cost.

Further, the first resolution may be determined based on the resolution of the first medical image in only some predetermined axis directions among the three axis directions, namely the X-axis, Y-axis, and Z-axis directions. The second resolution may be determined based on the resolution of the first medical image and/or the upper limit resolution in only some predetermined axis directions. In this case, the first and second resolutions may be determined as any predetermined values in an axis direction other than the predetermined axis directions.

(Generation of First and Second Subtraction Images)

In step S2050, the subtraction image generation unit 105 performs a first subtraction process between the first and second medical images with the first output resolution for cross section display determined in step S2040, thereby generating a first subtraction image having the first output resolution. Further, the subtraction image generation unit 105 performs a second subtraction process between the first and second medical images with the second output resolution for projection display determined in step S2040, thereby generating a second subtraction image having the second output resolution. Then, between the two generated subtraction images, the subtraction image generation unit 105 outputs the first subtraction image for cross section display to the display control unit 107 and outputs the second subtraction image for projection display to the projection image generation unit 106.

Generally, the generation of a subtraction image based on a subtraction process between the first and second medical images is performed by the following method. That is, based on the displacement field acquired in step S2030, with respect to each pixel on the first medical image, a position (coordinates) on the second medical image corresponding to the position (coordinates) of the pixel is calculated. Then, with respect to each pixel on the first medical image, the subtracted value between the pixel values at the corresponding positions (coordinates) is taken, thereby generating a subtraction image. Consequently, the position (coordinates) of each pixel on the subtraction image corresponds to the position (coordinates) of each pixel on the first medical image. Thus, the subtraction image can be acquired with the same resolution as the first medical image.

In the first subtraction process according to the present exemplary embodiment, the first output resolution is the same as the resolution of the first medical image. Thus, the first subtraction image is generated by executing the same subtraction process as above. On the other hand, in the second subtraction process, the second output resolution does not necessarily match the resolution of the first medical image. Thus, after the resolution of the first medical image is converted into the second output resolution first, a subtraction process similar to the above is executed, thereby generating the second subtraction image. That is, a process obtained by replacing the first medical image in the subtraction process method with the first medical image subjected to the resolution conversion is performed. Consequently, the position (coordinates) of each pixel on the second subtraction image corresponds to the position (coordinates) of each pixel on the first medical image subjected to the second output resolution. Thus, the second subtraction image can be acquired with the second output resolution. The methods for the subtraction processes according to the present exemplary embodiment are not limited to these. For example, in the second subtraction process, a method for not converting the resolution of the first medical image into the second output resolution first may be used. More specifically, an empty area for the second subtraction image having the second output resolution is prepared first. Then, with respect to the position (coordinates) of each pixel in the area, the subtracted value between the pixel values at a position (coordinates) on the first medical image originally associated with the position and a position (coordinates) on the second medical image associated with the position using the displacement field may be taken, thereby generating the second subtraction image.

FIG. 3 illustrates an axial cross section 300 of the first medical image, an axial cross section 301 of the second medical image, and an axial cross section 302 of the first subtraction image. A portion 303 in the axial cross section 300 of the first medical image represents an abnormal part. A portion 304 in the axial cross section 302 of the first subtraction image represents a subtraction area corresponding to the abnormal part 303. Since an abnormal part is not present in an area of the second medical image corresponding to the abnormal part 303 present in the first medical image, the subtraction area corresponding to the abnormal part 303 is an area visualized as the subtracted value between the intensities of these areas. At this time, the resolution of the first subtraction image matches the resolution of the first medical image. Thus, the images are associated with each other in a unit of a pixel. Thus, for example, corresponding positions between the images can be easily displayed such that, for example, the images are fused together, or the position of the corresponding original abnormal part 303 is displayed by specifying the subtraction area 304.

If the first and second output resolutions are the same as a result of comparison, for example, the first subtraction image may be generated by executing only the first subtraction process. Then, the second subtraction image may be acquired based on the first subtraction image. The method for acquiring the second subtraction image at this time may duplicate the first subtraction image, or may set the reference destination of the second subtraction image to the first subtraction image. Consequently, it is possible to avoid the situation where calculation cost is unnecessarily increased by executing the same subtraction process twice. Alternatively, conversely, the second subtraction image may be generated by executing only the second subtraction process. Then, the first subtraction image may be acquired based on the second subtraction image.

(Generation of Subtraction Projection Image or the Like)

In step S2060, the projection image generation unit 106 generates a subtraction projection image or the like obtained by two-dimensionally projecting the intensity value (pixel value) of the second subtraction image generated in step S2050. Then, the projection image generation unit 106 outputs the generated subtraction projection image or the like to the display control unit 107.

More specifically, the projection image generation unit 106 generates as the subtraction projection image a projection image obtained by projecting the second subtraction image that is a three-dimensional image, parallel to the slice plane. In a case where the original images of the second subtraction image are X-ray CT images, the slice directions match the body axis direction (the Z-axis). Thus, the subtraction projection image is an image projected in a direction orthogonal to the body axis of the subject. For example, the subtraction projection image projected in the front direction (the coronal direction) of the subject as a direction orthogonal to the body axis is generated. Consequently, it is possible to easily grasp information regarding a subtraction image of the entirety of an imaged part of the subject. As the projection method, for example, an image obtained by calculating the average value of the maximum value and the minimum value of the intensity in the projection direction is generated. Hereinafter, this image will be referred to as a "maximum intensity projection/minimum intensity projection (MIP/MinIP) image". Consequently, it is possible to reflect on the projection image a value obtained considering both a positive subtracted value and a negative subtracted value of the second subtraction image. The projection method is not limited to this method. Alternatively, MIP may be used, or MinIP may be used. Yet alternatively, a volume rendering image generated by any method may be used. Yet alternatively, a sagittal or coronal cross-sectional image or a slab MW image may be used. At this time, the resolution in the slice direction of the subtraction projection image is the second output resolution determined in step S2040.

FIG. 4 illustrates a coronal cross-sectional image 400 of the first medical image and a subtraction projection image 401. A portion 402 in the coronal cross-sectional image 400 of the first medical image represents an abnormal part. A portion 403 in the subtraction projection image 401 represents a subtraction projection area obtained by projecting a subtraction area corresponding to the abnormal part 402. This corresponds to an area obtained by projecting in the coronal direction a three-dimensional subtraction area including the subtraction area 304 on the slice image in FIG. 3. In FIG. 4, the slice interval of the first medical image is coarse (e.g., 5 mm). Thus, the resolution in the slice direction (the Z-axis in FIG. 4) of the coronal cross-sectional image 400 is coarse. The subtraction projection image 401, however, is an image that holds the amount of information of the subtraction in detail in which the resolution in the slice direction is the upper limit resolution (the processing resolution) (e.g., 1 mm), and therefore is not coarse in the slice direction. That is, since the slice interval of the first medical image is coarse, the abnormal part 402 is coarse on the coronal cross section 400. The subtraction projection area 403 in the subtraction projection image 401, however, holds the amount of information of the subtraction in detail and therefore is finely visualized.

An example has been taken where the subtraction projection image projected in the front direction of the subject as a direction orthogonal to the body axis is generated. In the present exemplary embodiment, a plurality of projection images is generated by performing a projection process while changing the projection direction by rotating around the body axis, including this direction. Then, a single piece of data is generated by putting a set of these projection images together. For ease of description, data of a set of individual projection images is also referred to as the "subtraction projection image". For example, set data composed of a total of 36 projection images obtained by dividing space around the body axis into 10° intervals is generated as the subtraction projection image. The method for generating the subtraction projection image is not limited to this method. Alternatively, the process of projecting the intensity value of the subtraction image from any direction may be used.

(Saving of Subtraction Image and Subtraction Projection Image)

In step S2070, the subtraction image generation unit 105 and the projection image generation unit 106 save the first subtraction image and the subtraction projection image, respectively, in a storage unit (not illustrated). Meanwhile, the saving of the second subtraction image from which the subtraction projection image is generated is restricted. In the restriction of the saving, specifically, the second subtraction image may not be saved in the storage unit, or may be only temporarily saved in the storage unit. If a plurality of types of storage units exists, the second subtraction image may be saved in only some of the storage units.

In a case where the second subtraction image is not saved in the storage unit, the subtraction projection image or the like is used for projection display, and the second subtraction image is not normally used. Thus, the saved amount of the storage unit can be reduced by this amount. In a case where the second subtraction image is only temporarily saved in the storage unit, for example, the second subtraction image is saved in the storage unit for a certain period (e.g., a week) after the second subtraction image is generated, but can be automatically deleted after the certain period elapses. Consequently, if the user wishes to output the subtraction projection image again by changing a parameter (e.g., the projection direction of the subtraction image), the user can save the trouble of generating the second subtraction image again because the second subtraction image is saved in the storage unit in the certain period. If a plurality of types of storage units exists, and for example, the storage units are a storage medium provided in the image processing apparatus 100 and a storage medium in the data server 130 such as a PACS, the second subtraction image is saved only in the storage medium in the image processing apparatus 100, but can be prohibited from being saved in the storage medium in the data server 130. Consequently, in the image processing apparatus 100, it is possible to generate the subtraction projection image again by changing a parameter (e.g., the projection direction of the subtraction image) based on the second subtraction image at any time. Meanwhile, only the initially generated subtraction projection image is saved in the data server 130, whereby it is possible to reduce the saved amount of data by saving minimum data for projection display. In a case where an increase in the saved amount can be allowed, the second subtraction image may be saved (without controlling the saving). In a case where the second subtraction image is saved, the process of step S2060 for generating the subtraction projection image or the like may be omitted.

(Display of Images)

In step S2080, the display control unit 107 performs control to display on the display unit 150 a cross-sectional image of the first subtraction image acquired from the subtraction image generation unit 105 and the subtraction projection image or the like acquired from the projection image generation unit 106. The display control unit 107 performs control to display cross-sectional images of the first and second medical images on the display unit 150.

Based on the above, the processing of the image processing apparatus 100 is performed.

According to the present exemplary embodiment, it is possible to generate a subtraction image having an appropriate resolution according to a cross section to be displayed. A subtraction image can be displayed in a cross-sectional manner on the same slice as original images, and in a case where a projection image obtained by projecting the intensity value (pixel value) of the subtraction image parallel to the slice plane is generated, it is possible generate the resolution in the slice direction as a fine resolution even in a case where the slice intervals of the original images are coarse. Consequently, in a case where a projection image obtained by projecting the intensity value (pixel value) of a subtraction image parallel to the slice plane is generated as in the above non-patent literature, it is possible to generate a high-visibility projection image having a fine resolution in the slice direction even in a case where the slice intervals of original images are coarse.

(Variations)

In the first exemplary embodiment, as an example, a case has been illustrated where the upper limit (the upper limit resolution) for determining the value of the second output resolution in the slice direction is matched to the processing resolution. The upper limit of the second output resolution and the processing resolution, however, may not necessarily be matched to each other. For example, the processing resolution may be determined as a value close to the upper limit of the second output resolution. In this variation, the close value is defined as a value within ±0.5 mm from a target resolution. That is, the close value is a value based on the upper limit resolution and including the upper limit resolution. For example, in step S2040, the upper limit of the output resolution is set to a resolution (1 mm) that enables the calculation of the subtraction in detail between images as described in step S2020. On the other hand, in step S2020, the processing resolution to which the resolution conversion is performed is set to 1.5 mm, which is a value close to 1 mm. Then, in step S2030, registration is performed between the first and second conversion images subjected to the resolution conversion to 1.5 mm. Consequently, the registration is performed with a resolution close to that used in a case where the first and second conversion images are subjected to the resolution conversion to 1 mm, whereby it is possible to perform registration at high speed by reducing the registration accuracy as little as possible (by reducing the amount of information of the displacement field as little as possible). Then, in step S2050, using the displacement field having a resolution of 1.5 mm, a subtraction image is generated under the condition that the upper limit of the second output resolution is 1 mm. In step S2070, a subtraction projection image based on the subtraction image is generated. At this time, in the displacement field used to generate the subtraction image, the amount of information is not reduced much as compared with the case of 1 mm. Thus, it is possible to generate the subtraction projection image without reducing the amount of information in the slice direction much. As described above, if the processing resolution is more coarse than, but has a value close to the upper limit of the second output resolution, it is possible to output the subtraction projection image at high speed by reducing quality as little as possible as compared with the subtraction projection image generated in the first exemplary embodiment.

Figure 6:
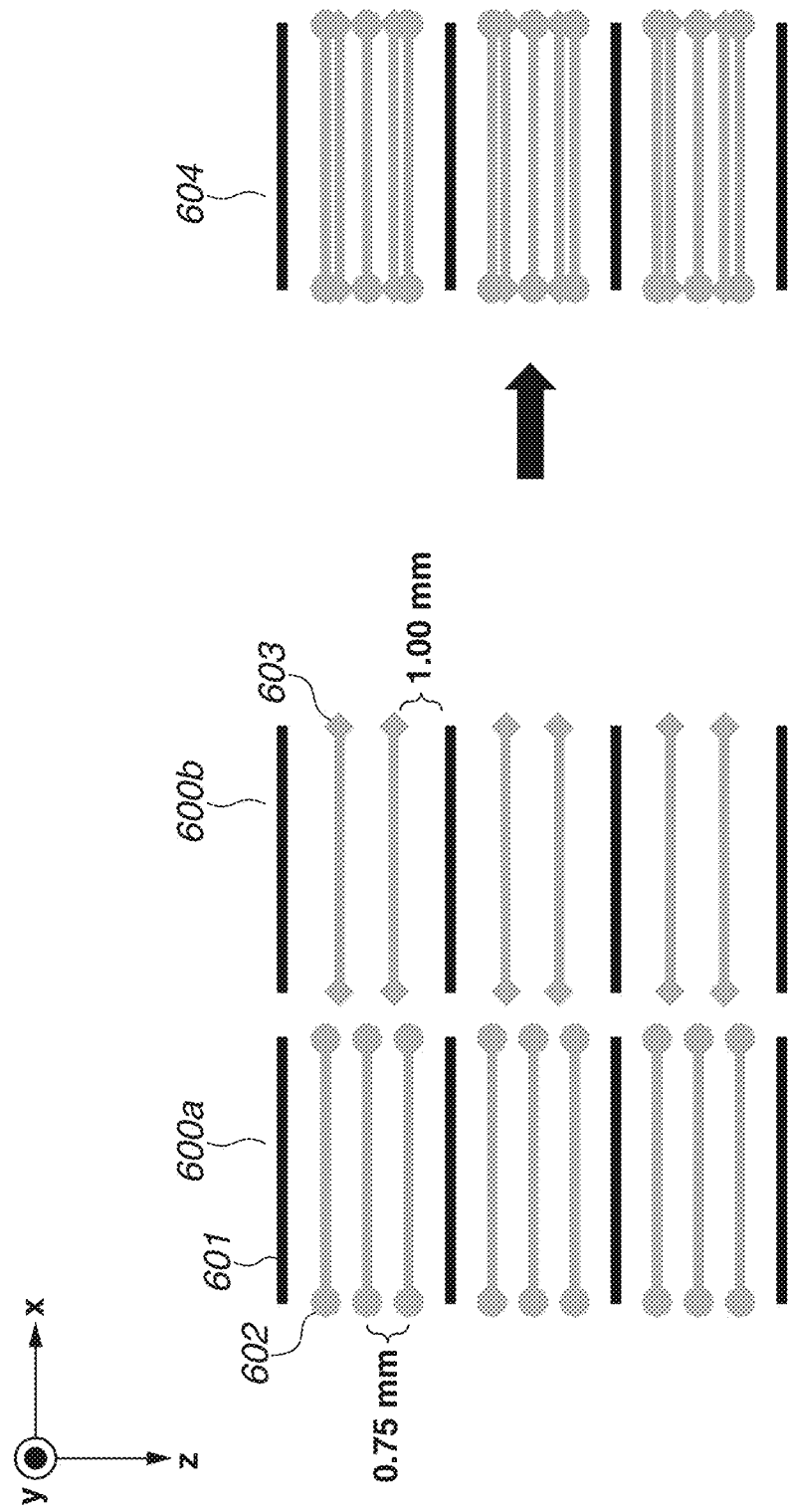
FIG. 6 is a diagram illustrating an example of a step of generating an inclusive subtraction image according to the first exemplary embodiment.

In the first exemplary embodiment, when the subtraction images are saved, the first subtraction image is saved as it is for cross section display, while the second subtraction image is used to only generate the subtraction projection image or the like. Thus, the saving of the second subtraction image is restricted to reduce the saved amount. In a second exemplary embodiment, when the subtraction images are saved, the saved amount is reduced taking into account both the first and second subtraction images. More specifically, data of a portion common to the first and second subtraction images is saved as common data, and pieces of data of portions that are not common to the first and second subtraction images are saved as pieces of specific data of the respective subtraction images such that the common data and the pieces of specific data are combined into a single piece of data. More specifically, as illustrated in FIG. 6, a two-dimensional tomographic image (a slice image) common to a first subtraction image 600a and a second subtraction image 600b that are three-dimensional images is common data 601. Among pieces of data that are not common to the first subtraction image 600a and the second subtraction image 600b, a two-dimensional tomographic image included in the first subtraction image 600a is stored as first specific data 602 in the storage unit, and a two-dimensional tomographic image included in the second subtraction image 600b is stored as second specific data 603 in the storage unit.

The processing according to the present exemplary embodiment is described below. The configuration of an information processing system according to the present exemplary embodiment is similar to that in FIG. 1, and therefore is not described here. The outline of the functions of steps in a flowchart illustrating the entirety of a processing procedure performed by the image processing apparatus 100 is similar to that in FIG. 2. Steps S2010 to S2060 and S2080 in the flowchart in FIG. 2 are similar to those in the first exemplary embodiment, and therefore are not described here. Only the differences from the first exemplary embodiment in the flowchart in FIG. 2 are described below.

(Saving of Subtraction Image and Subtraction Projection Image)

In step S2070, the subtraction image generation unit 105 generates an inclusive subtraction image including the first and second subtraction images and saves the inclusive subtraction image in the storage unit. The projection image generation unit 106 saves the subtraction projection image in the storage unit. For example, as illustrated in FIG. 6, the inclusive subtraction image includes the common data 601 common to the first subtraction image 600a and the second subtraction image 600b, and among pieces of data that are not common to the first subtraction image 600a and the second subtraction image 600b, the first specific data 602 included in the first subtraction image 600a and the second specific data 603 included in the second subtraction image 600b. That is, two-dimensional tomographic images included in the first subtraction image 600a that is a three-dimensional image and two-dimensional tomographic images included in the second subtraction image 600b that is a three-dimensional image are distinguished as a plurality of different pieces of data, and then, the plurality of pieces of data is put together and stored as an inclusive subtraction image 604 in the storage unit. That is, the subtraction image generation unit 105 corresponds to an example of a third generation unit configured to distinguish two-dimensional tomographic images included in the first and second subtraction images that are three-dimensional images, as two-dimensional tomographic images common to the first and second subtraction images and two-dimensional tomographic images that are not common to the first and second subtraction images, and configured to generate an inclusive subtraction image from, among the images common to the first and second subtraction images, a two-dimensional tomographic image of either one of the first and second subtraction images and two-dimensional tomographic images that are not common to the first and second subtraction images.

With reference to FIG. 6, the method for generating an inclusive subtraction image and storing the inclusive subtraction image in the storage unit is specifically described below.

First, as described in step S2040, since the resolution in the slice plane of a CT image is generally finer than 1 mm, the resolution in the slice plane of the first medical image does not normally exceed the upper limit resolution (1 mm). Thus, the resolution in the slice plane of the second output resolution is determined as the resolution of the first medical image. That is, the resolution in the slice plane of the second output resolution is the same as the first output resolution. Thus, the difference between the first and second output resolutions is substantially only the difference in the resolution in the slice direction (the slice interval).

Consequently, between the first subtraction image 600a and the second subtraction image 600b, pixels are associated with each other in the slice planes (the XY planes) having the same resolution. In response, each of the two subtraction images is layered in a unit of a slice in the slice direction (the Z-direction), whereby it is possible to generate a single volume. At this time, pieces of common data common to the first subtraction image 600a and the second subtraction image 600b are distinguished from other pieces of data, and only pieces of common data of either one of the first subtraction image 600a and the second subtraction image 600b (e.g., pieces of common data of the first subtraction image 600a) are layered, thereby preventing the redundancy of the same data.

In this case, even if the slice intervals of the first subtraction image 600a and the second subtraction image 600b are different from each other, the slice positions in the first subtraction image 600a and the second subtraction image 600b match each other at the slice position of the least common multiple of the slice intervals of the first subtraction image 600a and the second subtraction image 600b. For example, if the slice interval of the first subtraction image 600a is 0.75 mm, and the slice interval of the second subtraction image 600b is 1.0 mm, the least common multiple is 3.0 mm. Thus, the slice positions in the first subtraction image 600a and the second subtraction image 600b match each other at 3.0-mm intervals. Since the subtracted values at the same slice position in subtraction images having the same resolution in the slice planes match each other. Thus, this slice is common data common to the subtraction images. Then, with respect to each slice, a slice at the slice position of a multiple of 3.0 mm is assigned a label as the common data 601. A slice of the first subtraction image 600a that is not included in the common data 601 is assigned a label as the first specific data 602. Further, a slice of the second subtraction image 600b that is not included in the common data 601 is assigned a label as the second specific data 603. Then, the inclusive subtraction image 604 is generated by layering slice images of the first subtraction image 600a and the second subtraction image 600b. Consequently, the inclusive subtraction image 604 is represented as a single volume, but the three labels are assigned to the slice images. Thus, the inclusive subtraction image 604 can be separated into the first subtraction image 600a and the second subtraction image 600b again. As described above, common data common to the first subtraction image 600a and the second subtraction image 600b is prevented from being redundantly saved, whereby it is possible to reduce the saved amount in the storage unit. In a case where the slice intervals of two images match each other, all pieces of data of the two images are the same. Thus, all the pieces of data are pieces of common data, and only a single subtraction image is saved as an inclusive subtraction image.

All the slices except for redundant slices are saved as files on the slice-by-slice basis in a predetermined folder, a link to each slice of the first subtraction image 600a is placed in a folder of the first subtraction image, and a link to each slice of the second subtraction image 600b is placed in a folder of the second subtraction image, whereby it is possible to save both subtraction images by removing redundant data.

Based on the above, the processing of the image processing apparatus 100 is performed. The image data saved in step S2070 can be read by the following method. That is, regarding the first subtraction image, the common data and the first specific data are acquired and integrated together, whereby it is possible to acquire the original first subtraction image. Regarding the second subtraction image, the common data and the second specific data are acquired and integrated together, whereby it is possible to acquire the original second subtraction image. The subtraction projection image or the like can be generated again from the read second subtraction image by a method similar to that in step S2060. The read first subtraction image and the subtraction projection image or the like generated again can be displayed on the display unit 150 by a method similar to that in step S2080.

Based on the above, data common to the first and second subtraction images and pieces of data that are not common to the first and second subtraction images are distinguished from each other, and the common data of only either one of the subtraction images is saved, whereby it is possible to reduce the saved amount without reducing the amount of information of the acquired subtraction images. The inclusive subtraction image is generated and stored in the storage unit, whereby it is possible to reduce the saved amount. Thus, it is possible to store data without setting limitations on the saving periods and the saving locations of the first and second subtraction images.

Other Exemplary Embodiments

The technique according to the present invention can employ exemplary embodiments as, for example, a system, an apparatus, a method, a program, and a recording medium (a storage medium). Specifically, the technique according to the present invention may be applied to a system including a plurality of devices (e.g., a host computer, an interface device, an imaging apparatus, and a web application), or may be applied to an apparatus composed of a single device.

The purpose of the technique according to the present invention is achieved as follows. That is, a recording medium (or a storage medium) that records a program code (a computer program) of software for achieving the functions of the above exemplary embodiments is supplied to a system or an apparatus. This storage medium is a computer-readable storage medium. Then, a computer (or a central processing unit (CPU) or a microprocessor unit (MPU)) of the system or the apparatus reads and executes the program code stored in the recording medium. In this case, the program code itself read from the recording medium achieves the functions of the above exemplary embodiments, and the recording medium that records the program code constitutes the technique according to the present invention.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-119130, filed Jun. 26, 2019, which is hereby incorporated by reference herein in its entirety.

What is claimed is:

1. An image processing apparatus comprising:
an acquisition unit configured to acquire a first medical image and a second medical image that are three-dimensional images obtained by imaging a subject;
a determination unit configured to determine a first resolution based on a resolution of the first medical image and determine a second resolution based on a predetermined resolution;
a first generation unit configured to generate a first subtraction image having the first resolution by performing a first subtraction process between the first and second medical images, and generate a second subtraction image having the second resolution by performing a second subtraction process between the first and second medical images; and
a second generation unit configured to generate a projection image using the second subtraction image.

2. The image processing apparatus according to claim 1, further comprising:
a registration unit configured to perform registration between a first medical image subjected to resolution conversion and a second medical image subjected to resolution conversion, wherein the first medical image subjected to resolution conversion was generated by subjecting the first medical image to resolution conversion, and the second medical image subjected to resolution conversion was generated by subjecting the second medical image to resolution conversion; and
a display control unit configured to display at least one of the first medical image, the second medical image, the first subtraction image, and the projection image on a display unit,
wherein the first generation unit generates the first and second subtraction images using the first and second medical images subjected to the registration.

3. The image processing apparatus according to claim 1, further comprising a storage unit configured to store the first subtraction image and at least either one of the second subtraction image or the projection image in the storage unit.

4. The image processing apparatus according to claim 1, wherein the first generation unit generates the first subtraction image by performing the first subtraction process based on the first medical image subjected to conversion into the first resolution and the second medical image, and generates the second subtraction image by performing the second subtraction process based on the first medical image subjected to conversion into the second resolution and the second medical image.

5. The image processing apparatus according to claim 1, wherein in a case where the first and second resolutions match each other, the first generation unit generates the second subtraction image based on the first subtraction image.

6. The image processing apparatus according to claim 1, wherein the determination unit determines the resolution of the first medical image as the first resolution.

7. The image processing apparatus according to claim 1, wherein the determination unit determines the second resolution based on the resolution of the first medical image and the predetermined resolution.

8. The image processing apparatus according to claim 7, wherein the determination unit determines as the second resolution the higher of the resolution of the first medical image and the predetermined resolution.

9. The image processing apparatus according to claim 7, wherein the determination unit determines the second resolution based on the resolution of the first medical image, a resolution of the second medical image, and the predetermined resolution.

10. The image processing apparatus according to claim 9, wherein the determination unit determines as the second resolution the highest resolution among the resolution of the first medical image, the resolution of the second medical image, and the predetermined resolution.

11. The image processing apparatus according to claim 1,
wherein based on the resolution of the first medical image and/or the predetermined resolution, the determination unit determines the first and second resolutions in at least a predetermined axis direction among three axis directions different from one another in the three-dimensional images, and
wherein the first generation unit generates the first subtraction image in which a resolution in the predetermined axis direction is the first resolution, and the second subtraction image in which a resolution in the predetermined axis direction is the second resolution.

12. The image processing apparatus according to claim 11, wherein the predetermined axis direction is a body axis direction.

13. The image processing apparatus according to claim 1, wherein the predetermined resolution is a resolution suitable for displaying the projection image generated by projecting the second subtraction image in a direction orthogonal to a body axis of the subject.

14. The image processing apparatus according to claim 13, wherein the predetermined resolution has a predetermined value greater than or equal to 0.5 mm and less than or equal to 2.0 mm.

15. The image processing apparatus according to claim 3, wherein the storage unit stores the projection image in the storage unit and restricts storage of the second subtraction image in the storage unit.

16. The image processing apparatus according to claim 15, wherein the storage unit stores the second subtraction image in the storage unit only for a predetermined period.

17. The image processing apparatus according to claim 3, wherein the storage unit includes a plurality of storage media and stores the projection image and the second subtraction image in storage media different from each other among the plurality of storage media.

18. The image processing apparatus according to claim 3, further comprising a third generation unit configured to distinguish two-dimensional tomographic images included in the first and second subtraction images that are three-dimensional images, as two-dimensional tomographic images common to the first and second subtraction images and two-dimensional tomographic images that are not common to the first and second subtraction images, and configured to generate an inclusive subtraction image from, among the two-dimensional tomographic images common to the first and second subtraction images, a two-dimensional tomographic image of either one of the first and second subtraction images and two-dimensional tomographic images that are not common to the first and second subtraction images,
wherein the storage unit stores the inclusive subtraction image in the storage unit.

19. An image processing method comprising:
acquiring a first medical image and a second medical image that are three-dimensional images obtained by imaging a subject;
determining a first resolution based on a resolution of the first medical image and determining a second resolution based on a predetermined resolution;
generating a first subtraction image having the first resolution by performing a first subtraction process between the first and second medical images, and generating a second subtraction image having the second resolution by performing a second subtraction process between the first and second medical images; and
generating a projection image using the second subtraction image.

20. A non-transitory computer-readable storage medium that records a program for causing a computer to function as the units of the image processing apparatus according to claim 1.

21. An image processing apparatus comprising:
an acquisition unit configured to acquire a first medical image and a second medical image that are three-dimensional images obtained by imaging a subject;
a determination unit configured to determine a first resolution based on a resolution of the first medical image and determine a second resolution based on the first resolution;
a first generation unit configured to generate a first subtraction image having the first resolution by performing a first subtraction process between the first and second medical images, and generate a second subtraction image having the second resolution by performing a second subtraction process between the first and second medical images; and
a second generation unit configured to generate a projection image using the second subtraction image.

22. The image processing apparatus according to claim 21, wherein the determination unit determines a resolution equal to or higher than the first resolution as the second resolution.

* * * * *